US010765775B2

(12) United States Patent
Radisch et al.

(10) Patent No.: US 10,765,775 B2
(45) Date of Patent: Sep. 8, 2020

(54) IMPLANTABLE MEDICAL DEVICES COMPRISING BIO-DEGRADABLE ALLOYS WITH ENHANCED DEGRADATION RATES

(71) Applicants: Bio DG, Inc., Poway, CA (US); U.S. Department of Energy, Washington, DC (US)

(72) Inventors: Herbert Radisch, San Diego, CA (US); Paul Jablonski, Poway, CA (US)

(73) Assignees: Bio DG, Inc., Poway, CA (US); U.S. Department of Energy, Washington, DC (US)

( * ) Notice: Subject to any disclaimer, the term of this patent is extended or adjusted under 35 U.S.C. 154(b) by 0 days.

(21) Appl. No.: 16/255,093

(22) Filed: Jan. 23, 2019

(65) Prior Publication Data

US 2019/0374675 A1 Dec. 12, 2019

Related U.S. Application Data

(63) Continuation of application No. 14/213,855, filed on Mar. 14, 2014, now abandoned.

(60) Provisional application No. 61/785,531, filed on Mar. 14, 2013.

(51) Int. Cl.
| | |
|---|---|
| *A61L 27/04* | (2006.01) |
| *A61C 8/00* | (2006.01) |
| *A61L 31/14* | (2006.01) |
| *A61L 31/16* | (2006.01) |
| *A61L 31/02* | (2006.01) |

(52) U.S. Cl.
CPC .......... *A61L 27/042* (2013.01); *A61C 8/0012* (2013.01); *A61L 31/022* (2013.01); *A61L 31/148* (2013.01); *A61L 31/16* (2013.01); *Y10T 428/12292* (2015.01)

(58) Field of Classification Search
CPC ... A61C 8/0012; A61L 27/042; A61L 31/022; A61L 31/148; A61L 31/16; Y10T 428/12292
See application file for complete search history.

(56) References Cited

U.S. PATENT DOCUMENTS

| | | | |
|---|---|---|---|
| 5,425,769 A | 6/1995 | Snyders, Jr. | |
| 5,932,459 A | 8/1999 | Sittinger et al. | |
| 6,368,356 B1 | 4/2002 | Zhong et al. | |
| 6,649,631 B1 | 11/2003 | Orme et al. | |
| 6,783,727 B2 | 8/2004 | Bannykh et al. | |
| 7,268,205 B2 | 9/2007 | Williams et al. | |
| 7,601,230 B2 | 10/2009 | Craig | |
| 7,662,207 B2 | 2/2010 | Miura et al. | |
| 8,002,909 B2 | 8/2011 | Craig | |
| 8,241,654 B2 | 8/2012 | Stopek | |
| 8,246,762 B2 | 8/2012 | Janko et al. | |
| 8,591,672 B2 | 11/2013 | Janko et al. | |
| 9,084,843 B2 | 7/2015 | Guo et al. | |
| 2004/0138695 A1 | 7/2004 | Li et al. | |
| 2006/0020317 A1 | 1/2006 | Flach et al. | |
| 2006/0193742 A1 | 8/2006 | Miura et al. | |
| 2006/0229711 A1 | 10/2006 | Yan et al. | |
| 2007/0156231 A1 | 7/2007 | Weber | |
| 2007/0250155 A1 | 10/2007 | Simpson | |
| 2008/0015683 A1 | 1/2008 | Kramer-Brown et al. | |
| 2008/0069718 A1 | 3/2008 | Craig | |
| 2009/0198320 A1 | 8/2009 | Mueller et al. | |
| 2010/0076556 A1 | 3/2010 | Tomantschger et al. | |
| 2010/0324666 A1 | 12/2010 | Klocke et al. | |
| 2011/0022158 A1 | 1/2011 | Atanasoska et al. | |
| 2015/0152124 A1 | 6/2015 | Mori et al. | |
| 2019/0083683 A1 | 3/2019 | Janko et al. | |

FOREIGN PATENT DOCUMENTS

| | | |
|---|---|---|
| CN | 1781560 | 6/2006 |
| CN | 1685070 A | 10/2015 |
| EP | 1555332 A1 | 7/2005 |
| JP | 2006-026418 A | 2/2006 |
| WO | WO 2004/062707 A1 | 7/2004 |
| WO | WO 2004/073653 A2 | 9/2004 |
| WO | WO 2009/116799 A2 | 9/2009 |
| WO | WO 2010/080932 A2 | 7/2010 |

OTHER PUBLICATIONS

Examination Report issued in AU Application No. 2010203541 dated Nov. 29, 2013.
Extended European Search Report dated Jul. 11, 2016, for EP Application No. 14769061.4, filed on Mar. 14, 2014, 8 pages.
Hermawan et al., Development of degradable Fe-35Mn alloy for biomedical application, Advanced Mat. Res., vols. 15-17: 107-112, 2007.

(Continued)

*Primary Examiner* — Robert A Wax
*Assistant Examiner* — Olga V. Tcherkasskaya
(74) *Attorney, Agent, or Firm* — Cooley LLP

(57) ABSTRACT

The invention provides medical devices comprising high-strength alloys which degrade over time in the body of a human or animal, at controlled degradation rates, without generating emboli and which have enhanced degradation due to the presence of a halogen component. In one embodiment the alloy is formed into a bone fixation device such as an anchor, screw, plate, support or rod. In another embodiment the alloy is formed into a tissue fastening device such as staple. In yet another embodiment, the alloy is formed into a dental implant or a stent.

26 Claims, No Drawings

(56) References Cited

OTHER PUBLICATIONS

Hermawan et al., Iron-manganese: new class of metallic degradable biomaterials prepared by powder metallurgy, Powder Metallurgy, vol. 51[1]: 38-45, 2008.
International Preliminary Report on Patentability in International Application No. PCT/US2010/020396, dated Jul. 12, 2011, 6 pages.
International Search Report and Written Opinion for International Application No. PCT/US2010/020396, dated Sep. 29, 2010.
International Search Report and Written Opinion for International Application No. PCT/US2014/029290, dated Aug. 8, 2014, 17 pages.
Issel, Anne L Lim, Biocompatibility of Stent Materials, MURJ, vol. 11:33-37, 2004.
Office Action (and English translation) issued in CN Application No. 201080011031.7 dated May 10, 2013.
Supplementary European Search Report dated Feb. 21, 2014 in European Application No. 10729524.8.

IMPLANTABLE MEDICAL DEVICES COMPRISING BIO-DEGRADABLE ALLOYS WITH ENHANCED DEGRADATION RATES

CROSS-REFERENCE TO RELATED APPLICATION

This application is a continuation application of U.S. Application No. 14,213,855, filed on Mar. 14, 2014, which claims the benefit of and priority to U.S. Provisional Application No. 61/785,531, filed on Mar. 14, 2013, the contents of each which are hereby incorporated by reference in their entireties for all purposes.

FIELD OF THE INVENTION

The present invention relates to biodegradable materials useful for manufacturing implantable medical devices, specifically biodegradable compositions comprising iron reactive component containing metal alloys that can provide high strength when first implanted and are gradually eroded and replaced with body tissue.

BACKGROUND OF THE INVENTION

Medical devices meant for temporary or semi-permanent implant are often made from stainless steel. Stainless steel is strong, has a great deal of load bearing capability, is reasonably inert in the body, does not dissolve in bodily fluids, and is durable, lasting for many years, if not decades. Long lasting medical implants, however, are not always desirable. Many devices for fixing bones become problematic once the bone has healed, requiring removal by means of subsequent surgery. Similarly, short term devices such as tissue staples have to be removed after the tissue has healed, which limits their use internally.

Attempts to generate biodegradable materials have traditionally focused on polymeric compositions. One example is described in U.S. Pat. No. 5,932,459, which is directed to a biodegradable amphiphilic polymer. Another example is described in U.S. Pat. No. 6,368,356, which is directed to biodegradable polymeric hydrogels for use in medical devices. Biodegradable materials for use in bone fixation have been described in U.S. Pat. No. 5,425,769, which is directed to $CaSO_4$ fibrous collagen mixtures. And U.S. Pat. No. 7,268,205 describes the use of biodegradable polyhydroxyalkanoates in making bone fasteners such as screws. However, none of the biodegradable polymeric materials developed to date have demonstrated sufficient strength to perform suitably when substantial loads must be carried by the material, when the material is required to plastically deform during implantation, or when any of the other native characteristic of metal are required from the material. For example, the polyhydroxyalkanoate compositions described in U.S. Pat. No. 7,268,205 do not have sufficient strength on their own to bear weight and must be augmented by temporary fixation of bone segments. In addition, biodegradable polymeric materials tend to lose strength far more quickly than they degrade, because the portions of the material under stress tend to be more reactive, causing preferential dissolution and breakdown at load-bearing regions.

Metals, particularly steels, are thus preferred for the construction of many medical implants. The performance characteristics of steel closely match the mechanical requirements of many load bearing medical devices. Although ordinary steel compounds, unlike stainless steel, will degrade in biological fluids, they are not suitable for use in biodegradable implantable medical devices. This is because ordinary steels do not degrade in a predictable fashion, as one molecule or group of molecules at a time, which can be easily disposed of by the body. Rather, because of their large-grain structures, ordinary steels tend to break down by first degrading at grain boundaries, causing fissures and separations in the medical device, followed by rapid loss of strength and integrity and particulation. Particulation of the medical device is extremely dangerous because it allows small pieces of the device to leave the area of implantation and become lodged in other tissues, where they can cause serious injury including organ failure, heart attack and stroke. The use of ordinary steels in implantable medical devices is also complicated by the fact that ordinary steels typically contain alloying elements that are toxic when released in the body.

There remains a need in the field to develop additional implantable medical devices that have desirable characteristics associated with steel but which are also biodegradable.

SUMMARY OF THE INVENTION

The invention is based, in part, on the discovery that certain metal alloys having an iron reactive component will biodegrade over time without forming emboli. The invention is also based, in part, on the discovery that certain metal alloys having, e.g., an iron reactive component containing alloy which reacts with a bodily fluid when it is in contact with the fluid degrades with a degradation rate that is faster when implanted in a biological subject than the degradation rate of an alloy having the same composition except that the alloy does not contain an iron reactive component. Such alloys are useful for making biodegradable, implantable medical devices.

In some embodiments, the implantable medical device of the present invention comprises a biodegradable alloy, wherein the alloy is iron based and comprises an iron reactive component, wherein the alloy reacts with a bodily fluid when it is in contact with the fluid and wherein the degradation rate of the alloy when implanted in a biological subject is faster than the degradation rate of an alloy having the same composition as the said alloy except the absence of the iron reactive component.

In some embodiments, the iron reactive component has a boiling point above the melting temperature of an alloy having the same composition except the absence of the iron reactive component.

In some embodiments, the iron reactive component is a halogen component.

In some embodiments, the halogen component is provided as a salt. In some embodiments, the halogen component is selected from sodium fluoride, sodium chloride, copper chloride, copper fluoride, magnesium chloride, silver chloride, calcium chloride, calcium fluoride and iron chloride.

In some embodiments, the halogen component is selected from chloride, fluoride, bromide and iodide. In some embodiments, the halogen component is chloride or fluoride.

In some embodiments, the iron reactive component is in a salt form with a boiling temperature of at least about 1600° C., at least about 1650° C., at least about 1700° C., at least about 1750° C., at least about 1800° C., at least about 1850° C., at least about 1900° C., at least about 1950° C., or at least about 2000° C.

In some embodiments, the halogen component is halogen. In some embodiments, the halogen is chlorine.

In some embodiments, the iron reactive component is equally dispersed within the alloy.

In some embodiments, the iron reactive component is dispersed on the surface of the alloy.

In some embodiments, the implantable medical device of the present invention degrades at a rate of about 1-2 mg per day per square inch when placed in purified water.

In some embodiments, the average grain size is about 0.5 microns to about 5.0 microns. In some embodiments, the average grain size is stable at minimum recrystallization temperature of about 0.55 times the absolute melting temperature of the alloy.

In some embodiments, the implantable medical device is a bone screw, bone anchor, tissue staple, craniomaxillofacial reconstruction plate, fastener, reconstructive dental implant, or stent.

In some embodiments, the alloy comprises an austenite promoting component and a corrosion resisting component.

In some embodiments, the alloy contains between about 20% to 40% manganese. In some embodiments, the biodegradable alloy comprises manganese and niobium. In some embodiments, the alloy contains less than about 0.3% niobium. In some embodiments, the alloy contains less than about 1% carbon. In some embodiments, the biodegradable alloy comprises at least about 0.01% to about 0.1% non-metallic element. In some embodiments, the biodegradable alloy comprises at least about 0.01% to about 0.1% carbon.

In some embodiments, the implantable medical device is coated with a therapeutic agent.

In some embodiments, the implantable medical device is coated with a biodegradable hydrogel.

In some embodiments, the implantable medical device comprises a geometry that maximizes the surface to mass ratio.

In some embodiments, the implantable medical device comprises a hollow opening or passageway.

In some embodiments, the biodegradable alloy is formed by adding a gaseous iron reactive component during the melting process.

In some embodiments, the gaseous iron reactive component has a partial pressure of at least about 0.1 torr, at least about 0.2 torr, at least about 0.5 torr, at least about 0.8 torr, at least about 1 torr, at least about 2 torr, at least about 5 torr, at least about 10 torr, at least about 50 torr or at least about 100 torr.

In some embodiments, the iron reactive component is a halogen component.

In some embodiments, the halogen component is chlorine.

In some embodiments, the gaseous iron reactive component was added to mix with argon gas. In some embodiments, the argon gas has a partial pressure of at least about 10 torr, at least about 20 torr, at least about 50 torr, at least about 80 torr, at least about 100 torr, at least about 150 torr, at least about 200 torr, at least about 250 torr, at least about 300 torr, or at least about 500 torr.

The invention and additional embodiments thereof will be set forth in greater detail in the detailed description that follows.

Accordingly to some embodiments of the present invention, provided is a method of controlling the degradation rate of an implantable medical device, comprising a step of modulating the concentration of the iron reactive component in the alloy.

DETAILED DESCRIPTION OF THE INVENTION

As used herein, the term "percentage" when used to refer to the amount of an element in an alloy means a weight-based percentage. "Weighted percentages" of corrosion resisting and austenite promoting components, however, are calculated in a manner such that the weighted percentages do not necessarily correspond to the actual weight-based percentages.

The present invention is based, in part, on the discovery that certain metal alloys having, e.g., an iron reactive component containing alloy which reacts with a bodily fluid when it is in contact with the fluid degrades with a degradation rate that is faster when implanted in a biological subject than the degradation rate of an alloy having the same composition except that the alloy does not contain an iron reactive component. In some embodiments the alloys of the present invention have, for example, a fine-grain, substantially austenite structure that will biodegrade over time without forming emboli and that when these alloys contain an iron reactive component the degradation rate in human or animal body is enhanced. These austenite alloys exhibit little or no magnetic susceptibility and low magnetic permeability and can be made non-toxic and/or non-allergenic by controlling the amounts of various metals (e.g., chromium and nickel) incorporated into the alloys. In some embodiments the alloys of the present invention have, for example, a substantially martensite structure will biodegrade over time without forming emboli and that when these alloys contain an iron reactive component the degradation rate in human or animal body is enhanced. These martensite alloys can also be made non-toxic and/or non-allergenic by controlling the amounts of various metals (e.g., chromium and nickel) incorporated into the alloys. The alloys described herein may be incorporated into a variety of implantable medical devices that are used to heal the body of a subject (e.g., a human or other animal), but become unnecessary once the subject is healed. The alloys of the present invention can be used, for example, to make biodegradable, implantable medical devices that require high strength, such as bone fasteners for weight-bearing bones. The alloys can also be used to make biodegradable, implantable medical devices that require ductility, such as surgical staples for tissue fixation.

One object of the present invention is to provide medical devices for temporary implantation in the body of a subject (e.g., a human or animal subject), wherein the devices are made using a biodegradable alloy comprising an iron reactive component. The biodegradable alloy comprising an iron reactive component is one that is not a stainless steel, but instead undergoes reactions involving normal body chemistry to biodegrade or bio-absorb over time and will be removed by normal body processes. It is another object of the invention to provide implantable medical devices made using a biodegradable iron reactive component containing alloy that is non-toxic and/or non-allergenic as it is degrading and being processed by the body. It is yet another object of the invention to provide implantable medical devices made using a biodegradable alloy comprising an iron reactive component that has little or no magnetic susceptibility and low magnetic permeability and does not distort MRI images.

The iron reactive component can be added to the alloy by a variety of means known in the art. In some embodiments, the iron reactive component is capable of being equally dispersed throughout the alloy. In some embodiments, the iron reactive component is equally dispersed throughout the alloy.

In some embodiments, an iron reactive component is added at the time of melting of an alloy mixture or at anytime during the melting process. For example, the iron reactive component can be added later in the melting process, prior to the melt being poured into a mold. The iron reactive component can also be dispersed on the surface of the alloy. Such alloys can be generated by a variety of methods known in the art, including for example ion implantation. Ion implantation is well known and involves the process by which ions of a material are accelerated in an electrical field and impacted onto a solid surface, such as for example an alloy of the present invention. In some embodiments, the iron reactive component is dispersed on the surface of the alloy. In some embodiments, the iron reactive component is applied to the exterior surface of the alloy. In some embodiments, the iron reactive component is added to the alloy by methods of ion-implanting. See, e.g., Hamm, Robert W.; Hamm, Marianne E., Industrial Accelerators and Their Applications. World Scientific (2012). An iron reactive component of the present invention can include any component which provides for an enhanced alloy degradation rate when the alloy comprising the iron reactive component is exposed to a biological environment (i.e., implanted in a biological subject), as compared to the same alloy absent the iron reactive component. In some embodiments, the alloy comprises more than one iron reactive component.

According to one aspect of the present invention, small amounts of iron reactive components are useful for controlling the biodegradation rate of suitable alloys. In some embodiments, the concentration of the iron reactive component in the alloy is between about 0.1 ppm to about 1000 ppm, between about 0.1 ppm to about 800 ppm, between about 0.1 ppm to about 600 ppm, between about 0.1 ppm to about 400 ppm, between about 0.1 ppm to about 300 ppm, between about 0.1 ppm to about 250 ppm, between about 0.1 ppm to 200 ppm, between about 0.1 ppm to about 150 ppm, between about 0.1 ppm to about 100 ppm, between about 0.1 ppm to about 75 ppm, between about 0.1 ppm to about 50 ppm, between about 0.1 ppm to about 25 ppm or between about 0.1 ppm to about 10 ppm. In some embodiments, the concentration of the iron reactive component in the alloy is between about 1 ppm to 500 ppm, between about 10 ppm to about 300 ppm, or between about 50 ppm to about 150 ppm.

In some embodiments, the iron reactive component is stable at temperatures greater than or equal to the melting point of the alloy in the absence of the iron reactive component. In some embodiments, the iron reactive component is provided as a salt with a boiling temperature of at least about 1600° C., at least about 1650° C., at least about 1700° C., at least about 1750° C., at least about 1800° C., at least about 1850° C., at least about 1900° C., at least about 1950° C., or at least about 2000° C.

In some embodiments, the iron reactive component is provided as a gas during the fabrication process with a total or partial pressure of at least about 0.1 torr, at least about 0.2 torr, at least about 0.5 torr, at least about 0.8 torr, at least about 1 torr, at least about 2 torr, at least about 5 torr, at least about 10 torr, at least about 50 torr or at least about 100 torr.

In some embodiments, the iron reactive component is a halogen component. Halogen components of the present invention include halogens and/or the salt forms such as chloride, fluoride, bromide and iodide. In some embodiments, the halogen component is chlorine. In some embodiments, the halogen component is chloride or fluoride. In some embodiments the halogen component is chloride. In some embodiments the halogen component is fluoride. In some embodiments, the halogen component is stable at temperatures greater than or equal to the melting point of the alloy. In some embodiments, the alloy containing the iron reactive component comprises more than one halogen component.

In some embodiments, the iron reactive component is halogen containing salt. The halogen component can be provided to the alloy mixture as a salt during the process of generating the alloy. In some embodiments, the halogen containing salt is selected from sodium fluoride, sodium chloride, copper chloride, copper fluoride, silver chloride, calcium chloride, calcium fluoride and iron chloride. In some embodiments, mixtures of salts can be employed.

In some embodiments, a halogen containing salt is added to the alloy mixture at the time of melting or at anytime during the melting process. Any halogen containing salt with a boiling temperature greater than the melting temperature of the alloy can be used with the methods of the present invention. In some embodiments, the halogen component is provided as a salt with a boiling temperature of at least about 1600° C., at least about 1650° C., at least about 1700° C., at least about 1750° C., at least about 1800° C., at least about 1850° C., at least about 1900° C., at least about 1950° C., or at least about 2000° C. In some embodiments, the halogen component is stable at temperatures greater than or equal to the melting point of the alloy. In some embodiments, more than one halogen component can be employed.

Additionally or alternatively, a gaseous iron reactive component can be used during the process of generating the alloy. In some embodiments, the halogen component is chlorine gas. In some embodiments, the halogen component is provided as a gas with a total or partial pressure greater than or equal to about 0.1 torr, about 0.2 torr, about 0.5 torr, about 0.8 torr, about 1 torr, about 2 torr, about 5 torr, about 10 torr, about 50 torr or about 100 torr. In some embodiments, the total or partial pressure of the halogen component is a range of about 0.1 torr to about 100 torr, about 0.5 torr to about 50 torr, or about 1 to about 5 torr.

In some embodiments, mixtures of gases can be employed. Without being bound to any particular theory, it is contemplated that the amount of the iron reactive component can be fine tuned by controlling a partial pressure of the iron reactive component with or without additional gases. In some embodiments, an inert gas such as argon can be provided in a mixture with one or more halogen gases. In some embodiments, the argon gas has a partial pressure of at least about 10 torr, at least about 20 torr, at least about 50 torr, at least about 80 torr, at least about 100 torr, at least about 150 torr, at least about 200 torr, at least about 250 torr, at least about 300 torr, or at least about 500 torr. As demonstrated in Example 2, approximately 1 torr of chlorine can be added into 200 torr of argon during the melt process.

In some embodiments, the concentration of the halogen component in the alloy is between about 0.1 ppm to about 500 ppm, between about 0.1 ppm to about 400 ppm, between about 0.1 to about 300 ppm, between about 0.1 to about 250 ppm, between about 0.1 to about 200 ppm, between about 0.1 ppm to about 150 ppm, between about 0.1 to about 100 ppm, between about 0.1 ppm to about 75 ppm, between about 0.1 ppm to about 50 ppm, between about 0.1 to about 25 ppm or between about 0.1 ppm to about 10 ppm. In some embodiments, the halogen component in the alloy comprises between about 0.1 ppm to about 100 ppm.

Accordingly, in one aspect, the invention provides implantable medical devices comprising a biodegradable alloy that dissolves from its exterior surface. As used herein, the term "alloy" means a mixture of chemical elements comprising two or more metallic elements. Biodegradable alloys suitable for making implantable medical devices of the invention can be, for example, iron alloys (e.g., steels). In certain embodiments, the iron alloys comprise about 55% to about 65%, about 57.5% to about 67.5%, about 60% to about 70%, about 62.5% to about 72.5%, about 65% to about 75%, about 67.5% to about 77.5%, about 70% to about 80%, about 72.5% to about 82.5%, or about 75% to about 85% iron. The iron alloys further comprise one or more non-iron metallic elements. The one or more non-iron metallic elements can include, for example, transition metals, such as manganese, cobalt, nickel, chromium, molybdenum, tungsten, tantalum, niobium, titanium, zirconium, hafnium, platinum, palladium, iridium, rhenium, osmium, rhodium, etc., or non-transition metals, such as aluminum. In some embodiments, the iron alloys comprise at least two non-iron metallic elements. The at least two non-iron elements can be present in an amount of at least about 0.5% (e.g., at least about 1.0%, about 1.5%, about 2.0%, about 2.5%, about 3.0%, about 4.0%, about 5.0%, or more). In certain embodiments, the iron alloys comprise at least two non-iron metallic elements, wherein each of said at least two non-iron elements is present in an amount of at least about 0.5%, and wherein the total amount of said at least two elements is at least about 15% (e.g., at least about 17.5%, about 20%, about 22.5%, about 25%, about 27.5%, about 30%, about 32.5%, about 35%, about 37.5%, or about 40%). The biodegradable alloys can also comprise one or more non-metallic elements. Suitable non-metallic elements include, for example, carbon, nitrogen, and silicon. In certain embodiments, the iron alloys comprise at least about 0.01% (e.g., about 0.01% to about 0.10%, about 0.05% to about 0.15%, about 0.10% to about 0.20%, about 0.15% to about 0.25%, or about 0.20% to about 0.30%) of at least one non-metallic element.

Biodegradable alloys suitable for use in the implantable medical devices of the invention are designed to degrade from the outside inward, such that they maintain their strength for a greater portion of their life and do not particulate or embolize. Without intending to be bound by theory, it is believed that this is accomplished by providing an alloy structure that either has no appreciable reactive grain boundaries, forcing degradation to take place at the surface molecular layer, or by providing a very fine grain alloy that acts as a homogeneous, grain free material. In certain embodiments, the rate of dissolution from an exterior surface of a suitable biodegradable alloy is substantially uniform at each point of the exterior surface. As used herein in this context, "substantially uniform" means that the rate of dissolution from a particular point on an exterior surface is +/−10% of the rate of dissolution at any other point on the same exterior surface. As persons skilled in the art will appreciate, the type of "exterior surface" contemplated in these embodiments is one that is smooth and continuous (i.e., substantially planar, concave, convex, or the like) and does not include sharp edges or similar such discontinuities, as those are locations where the rate of dissolution is likely to be much higher. A "substantially" planar, concave, or convex surface is a surface that is planar, concave, convex, or the like and does not contain any bumps, ridges, or grooves that rise above or sink below the surface by more than 0.5 mm.

Steel alloys have iron as their primary constituent. Depending upon a combination of (i) the elements alloyed with the iron and (ii) the historical working of the alloy, steels can have different structural forms, such as ferrite, austenite, martensite, cementite, pearlite, and bainite. In some instances, steels having the same composition can have different structures. For example, martensite steel is a form of high tensile steel that can be derived from austenite steel. By heating austenite steel to between 1750° F. and 1950° F., and then rapidly cooling it to below the martensite transition temperature, the face centered cubic structure of the austenite steel will reorient into a body centered tetragonal martensite structure, and the martensite structure will freeze into place. Martensite steel does not have appreciable grain boundaries, and thus provides no primary dissolution path to the interior of the steel. The result is a slow dissolution from the outside, without the formation of emboli. Metallurgical examination of martensitic material will show "pre-austenitic grain boundaries," places where the austenite grain boundaries once existed, but these are nonreactive traces of the former structure.

Accordingly, in certain embodiments, the biodegradable implantable medical devices of the invention comprise an alloy containing an iron reactive component (e.g., an iron alloy) having a substantially martensite structure. As used herein, the term "substantially martensite structure" means an alloy having at least 90% martensite structure. In certain embodiments, the alloy has at least 91%, 92%, 93%, 94%, 95%, 96%, 97%, 98%, 99%, 99.5%, 99.8%, 99.9% A or more martensite structure.

The martensite alloy can have the composition of any alloy described herein. For example, in certain embodiments, the martensite alloy is formed from an austenite alloy described herein. In certain embodiments, the martensite alloy comprises carbon, chromium, nickel, molybdenum, cobalt, or a combination thereof. For example, in certain embodiments, the martensite alloy comprises (i) carbon, (ii) chromium and/or molybdenum, and (iii) nickel and/or cobalt. In certain embodiments, the martensite alloy comprises about 0.01% to about 0.15%, about 0.05% to about 0.20%, about 0.10% to about 0.25%, about 0.01% to about 0.05%, about 0.05% to about 0.10%, about 0.10% to about 0.15%, or about 0.15% to about 0.20% carbon. In certain embodiments, the martensite alloy comprises about 0.1% to about 6.0%, about 1.0% to about 3.0%, about 2.0% to about 4.0%, about 3.0% to about 5.0%, or about 4.0% to about 6.0% chromium. In certain embodiments, the martensite alloy comprises about 0.1% to about 6.0%, about 0.5% to about 2.5%, about 1.0% to about 3.0%, about 1.5% to about 3.5%, about 2.0% to about 4.0%, about 2.5% to about 4.5%, about 3.0% to about 5.0%, about 3.5% to about 5.5%, or about 4.0% to about 6.0% molybdenum. In certain embodiments, the martensite alloy comprises about 5.0% to about 9%, about 6.0% to about 10%, about 7.0% to about 11%, about 8.0% to about 12%, about 9.0% to about 13%, about 10% to about 14%, or about 11% to about 15% nickel. In certain embodiments, the martensite alloy comprises about 5.0% to about 10%, about 7.5% to about 12.5%, about 10% to about 15%, about 12.5% to about 17.5%, or about 15% to about 20% cobalt.

In certain embodiments, the martensite alloy contains about 2.0% to about 6.0%, about 3.0% to about 7.0%, about 3.5% to about 7.5%, about 4.0% to about 8.0%, about 4.5% to about 8.5%, or about 5.0% to about 9.0% of a corrosion resisting component. In certain embodiments, the martensite alloy contains about 2.5%, about 3.0%, about 3.5%, about 4.0%, about 4.5%, about 5.0%, about 5.5%, or about 6.0% of a corrosion resisting component. In certain embodiments, the corrosion resisting component is calculated as a sum of the percentages of corrosion resisting elements (e.g., chromium, molybdenum, tungsten, tantalum, niobium, titanium, zirconium, hafnium, etc.) in the alloy. In other embodiments, the corrosion resisting component is calculated as a weighted sum of the corrosion resisting elements in the alloy. In certain embodiments, individual elements in the weighted sum are weighted according to their corrosion resisting efficacy, as compared to chromium. In certain embodiments, the weighted % corrosion resisting component is determined according to the formula: % chromium+% molybdenum+% tungsten+0.5×(% tantalum+% niobium)+2×(% titanium+% zirconium+% hafnium).

In certain embodiments, the martensite alloy contains at least about 10%, about 15%, about 18%, about 20%, about 22%, or about 24% of an austenite promoting component. For example, in certain embodiments, the martensite alloy contains about 10% to about 20%, about 15% to about 25%, about 20% to about 30%, about 25% to about 35%, about 30% to about 40% of an austenite promoting component. In certain embodiments, the martensite alloy comprises about 22%, about 23%, about 24%, about 25%, about 26%, about 27%, or about 28% of an austenite promoting component. In certain embodiments, the austenite promoting component is calculated as a sum of the percentages of austenite promoting elements (e.g., nickel, manganese, cobalt, platinum, palladium, iridium, aluminum, carbon, nitrogen, silicon, etc.) in the alloy. In other embodiments, the austenite promoting component is calculated as a weighted sum of all the austenite promoting elements in the alloy. In certain embodiments, individual elements in the weighted sum are weighted according to their austenite promoting efficacy, as compared to nickel. In certain embodiments, the weighted % austenite promoting component is calculated according to the formula: % nickel+% platinum+% palladium+% iridium+0.5×(% manganese+% cobalt)+30×(% carbon+% nitrogen).

In certain embodiments, the martensite alloy comprises about 2.0% to about 4.0%, about 3.0% to about 5.0%, or about 4.0% to about 6.0% of a corrosion resisting component, and about 10% to about 20%, about 15% to about 25%, about 20% to about 30%, about 25% to about 35%, or about 30% to about 40% of an austenite promoting component. For example, in certain embodiments, the martensite alloy comprises about 3.0% to about 5.0% of a corrosion resisting component and about 20% to about 30% of an austenite promoting component. In certain embodiments, the corrosion resisting and austenite promoting components are calculated as sums of the percentages of corrosion resisting and austenite promoting elements, respectively. In other embodiments, the corrosion resisting and austenite promoting components are calculated as weighted sums of the corrosion resisting and austenite promoting elements, respectively.

While martensite alloys have the desirable characteristic of lacking grain boundaries, austenite alloys are particularly useful for medical implants because of their low magnetic susceptibility, which can be useful where the alloy is exposed to a strong magnetic field. It is desirable for medical implants to have low magnetic susceptibility because they may be used in patients that would have future need of Magnetic Resonance Imaging (MRI), which utilizes very high magnetic fields. A magnetic reactive alloy in a strong magnetic field can experience heating, causing local tissue stress and damage to tissue surrounding the implant. Magnetic reactive implants also distort MRI images, making them unreadable. In addition, austenite alloys can provide certain mechanical benefits, since they undergo larger plastic deformations between their elastic limit (yield point) and ultimate failure, as compared to martensite alloys. For example, whereas a martensite alloy may have a maximum elongation of about 16% to 20%, an austenite alloy can have a maximum elongation of about 50% to 60%.

Thus, in certain embodiments, the biodegradable implantable medical devices of the invention comprise an iron reactive component containing alloy (e.g., an iron alloy) having a substantially austenite structure. As used herein, the term "substantially austenite structure" means at least 85% austenite structure. In certain embodiments, the alloy has at least 88%, 90%, 91%, 92%, 93%, 94%, 95%, 96%, 97%, 98%, 99%, 99.5%, 99.8%, 99.9% or more austenite structure. In certain embodiments, the austenite alloy has substantially no martensite or ferrite structure. As used herein, the term "substantially no martensite or ferrite structure" means less than 5% (e.g., less than 4%, 3%, 2%, 1%, 0.5%, 0.2%, 0.1%, or 0.05%) martensite or ferrite structure. In certain embodiments, the austenite alloy is characterized by a maximum elongation of about 40% to about 65% (e.g., about 50% to about 60%).

Austenitic steels have grains with defined boundaries of irregular shape. Since austenite is a face centered cubic structure, the grains tend to be cubic when viewed perpendicular to a major lattice plane. In austenite alloys having either very low carbon or very low chromium, it is possible to create a structure with a fine grain size (e.g., about 0.5 microns to about 5.0 microns on a side). A cubic austenite grain of 2.5 microns has a total surface area of 37.5 square microns and a volume of 15.625 cubic microns, for a surface to volume ratio of $2.4\mu^{-1}$ and a total mass of 0.12 micrograms. Because of the extremely small mass of the grain, the grain material reacts as quickly as the grain boundary material when placed in a biological environment, allowing the alloy to shed material from the outside. This, in turn, prevents weakening of the material bulk along grain boundaries and grain separation from the material bulk of the alloy. As the size of grains increase, however, the ratio of surface to volume decreases. Each grain becomes bigger, taking longer to be absorbed, making it more likely that dissolution will take place along grain boundaries, penetrating deeper into the alloy's material bulk and thereby reducing the strength of the alloy.

The rate of biodegradation of iron reactive component containing alloys of the present invention can be further altered by controlling the grain size and surface to volume ratio of the individual grains. As the grain size increases, with a commensurate decrease in the surface-to-volume ratio, biodegradation progresses faster toward the center of the device, increasing the total biodegradation rate. However, too large a grain size can cause separation of grains and adverse effects.

In some embodiments the alloy containing the iron reactive component is an austenite alloy. In certain embodiments, the austenite alloy has an average grain size of about 0.5 microns to about 20 microns on each side. For example, in certain embodiments, the average grain size is about 0.5 microns to about 5.0 microns, about 2.5 microns to about 7.5 microns, about 5.0 microns to about 10 microns, about 7.5 microns to about 12.5 microns, about 10 microns to about 15 microns, about 12.5 microns to about 17.5 microns, or about 15 microns to about 20 microns on each side. In certain embodiments, the average grain size is about 0.5 to about 3.0 microns, or about 1.0 micron to about 2.0 microns on each side. In certain embodiments, the austenite alloy has a structure wherein the surface to volume ratio of individual grains is, on average, greater than $0.1\mu^{-1}$. For example, in certain embodiments, the surface to volume ratio of individual grains is, on average, greater than $0.2\mu^{-1}$, $0.3\mu^{-1}$, $0.4\mu^{-1}$, $0.5\mu^{-1}$, $0.6\mu^{-1}$, $0.7\mu^{-1}$, $0.8\mu^{-1}$, $0.9\mu^{-1}$, $1.0\mu^{-1}$, $1.5\mu^{-1}$, $2.0\mu^{-1}$, $2.5\mu^{-1}$, $3.0\mu^{-1}$, $3.5\mu^{-1}$, $4.0\mu^{-1}$, $4.5\mu^{-}$, $5.0\mu^{-1}$, $6.0\mu^{-1}$, $7.0\mu^{-1}$, $8.0\mu^{-1}$, $9.0\mu^{-1}$, $10.0\mu^{-1}$, $11.0\mu^{-1}$, $12.0\mu^{-1}$, $13.0\mu^{-1}$, $14.0\mu^{-1}$, $15.0\mu^{-1}$, or more.

Austenite grain sizes of about 0.5 microns to about 20 microns can be achieved by successive cycles of mechanical working to break down the alloy, followed by thermal recrystallization. The mechanical working of materials, whether done at cold temperatures (i.e. room temperature to 200° C.) or at elevated temperatures, causes strain-induced disruption of the crystal structure, by physically forcing the alloy into a new shape. The most common method of mechanical working of metals is by reducing the thickness of a sheet of metal between two high pressure rolls, causing the exiting material to be substantially thinner (e.g., 20%-60% thinner) than the original thickness. Other methods such as drawing can also be employed. The process of mechanically working metals breaks down larger, contiguous lattice units into different structures. More importantly, it stores substantial strain-induced energy into distorted lattice members, by straining lattice structure distances to higher energy arrangements. Subsequent low-temperature recrystallization, which takes place at about 0.35 to about 0.55 times the absolute melting temperature of the alloy, allows the lattice structure to undergo rearrangements to a lower energy condition, without changes to overall macro dimensions. To accommodate lattice rearrangement without gross changes in dimensions, the size of individual lattice sub-units, or grains, is reduced, releasing substantial strain energy by breaking the lattice into smaller sub-units, and producing a finer grain structure. The process of mechanical working followed by recrystallization can be repeated serially, producing finer and finer grains.

In certain embodiments, the austenite alloy comprises carbon. For example, in certain embodiments, the alloy comprises about 0.01% to about 0.10%, about 0.02% to about 0.12%, about 0.05% to about 0.15%, about 0.07% to about 0.17%, about 0.10% to about 0.20%, about 0.12% to about 0.22%, or about 0.15% to about 0.25% carbon. In certain embodiments, the austenite alloy comprises one or more (e.g., two or more) elements selected from the list consisting of nickel, cobalt, aluminum, and manganese. In certain embodiments, the alloy comprises about 2.0% to about 6.0%, about 3.0% to about 7.0%, about 4.0% to about 8.0%, or about 5.0% to about 9.0% nickel. In other embodiments, the alloy comprises substantially no nickel. In certain embodiments, the alloy comprises about 10% to about 20%, about 15% to about 20%, about 15% to about 25%, about 18% to about 23%, about 20% to about 25%, or about 20% to about 30% cobalt. In certain embodiments, the alloy comprises less than about 5.0% (e.g., less than about 4.5%, about 4.0%, about 3.5%, about 3.0%, or about 2.5%) manganese. In certain embodiments, the alloy comprises about 0.5% to about 1.5%, about 1.0% to about 2.0%, or about 1.5% to about 2.5% manganese. In other embodiments, the alloy comprises about 1.0% to about 8.0%, about 6.0% to about 10%, about 8.0% to about 12%, or about 10% to about 14% manganese. In other embodiments, the alloy comprises about 10% to about 50%, about 15% to about 45%, about 20% to about 40%, about 25% to about 35%, or about 25% to about 30% manganese. In certain embodiments, the austenite alloy comprises one or more (e.g., two or more) elements selected from the list consisting of chromium, molybdenum, and tantalum. In certain embodiments, the alloy comprises about 0.5% to about 1.5%, about 1.0% to about 2.0%, about 1.5% to about 2.5%, or about 2.0% to about 3.0% chromium. In other embodiments, the alloy comprises substantially no chromium. In certain embodiments, the alloy comprises about 0.5% to about 1.5%, about 1.0% to about 2.0%, about 1.5% to about 2.5%, or about 2.0% to about 3.0% molybdenum. In certain embodiments, the alloy comprises about 1.0% to about 3.0%, about 2.0% to about 4.0%, about 3.0% to about 5.0%, or about 4.0% to about 6.0% tantalum. In certain embodiments, the austenite alloy comprises (i) carbon, (ii) at least two elements selected from the list consisting of nickel, cobalt, aluminum, and manganese, and (iii) at least two elements selected from the list consisting of chromium, molybdenum, and tantalum.

Aside from the pattern of dissolution, the rate of dissolution and the release of potentially toxic elements needs to be controlled in alloys used to make implantable medical devices of the invention. The particular elements used to make up an alloy help determine the physical and chemical properties of the resulting alloy. For example, adding small amounts of carbon to iron changes the structure of the iron, creating steel that is greatly increased in hardness and strength, while changing the plasticity relative to iron. Similarly, stainless steels are fabricated by adding elements to the iron that decrease corrosion (i.e., corrosion resisting components), such as chromium and molybdenum. A stainless steel that resists corrosion in a biological system can contain, for example, 18% chromium and 1% molybdenum. Titanium, niobium, tantalum, vanadium, tungsten, zirconium, and hafnium likewise provide a protective effect that slows down the rate of degradation of steel in a biologic system.

A stainless steel that does not break down in the intended biological system is typically not suitable for use in a biodegradable implant. Thus, alloys having large quantities of corrosion resisting elements, such as chromium, molybdenum, titanium, and tantalum, usually cannot be used to make biodegradable implantable medical devices of the invention. However, small quantities of such corrosion resisting elements are useful for controlling the biodegradation rate of suitable alloys. Accordingly, in certain embodiments, an alloy useful for making a biodegradable implantable medical device of the invention (e.g., an austenite alloy) contains at least about 0.5%, about 1.0%, about 1.5%, about 2.0%, about 2.5%, about 3.0%, or about 3.5%, but less than about 15%, about 12%, about 11%, about 10%, about 9.0%, about 8.0% or about 7.0% of a corrosion resisting component. For example, in certain embodiments, the alloy contains about 1.0% to about 7.0%, about 2.0% to about 8.0%, or about 3.0% to about 9.0% of a corrosion resisting component. In certain embodiments, the alloy (e.g., austenite alloy) contains about 3.0%, about 3.5%, about 4.0%, about 4.5%, about 5.0%, about 5.5%, about 6.0%, about 6.5%, or about 7.0% of a corrosion resisting component. In certain embodiments, the corrosion resisting component is calculated as a sum of the percentages of corrosion resisting elements (e.g., chromium, molybdenum, tungsten, tantalum, niobium, titanium, zirconium, hafnium, etc.) in the alloy. In other embodiments, the corrosion resisting component is a weighted sum of all the corrosion resisting elements in the alloy. For example, in certain embodiments, individual elements in the weighted sum are weighted according to their corrosion resisting efficacy, as compared to chromium. In certain embodiments, the weighted % corrosion resisting component is determined according to the formula: % chromium+% molybdenum+% tungsten+0.5×(% tantalum+% niobium)+2×(% titanium+% zirconium+% hafnium).

Corrosion resisting elements, such as chromium and molybdenum, are ferrite promoting and tend to cause steel to form a ferritic structure. To overcome such ferrite promotion and achieve an austenite structure, austenite promoting elements can be added to the alloy. Austenite promoting elements include, for example, nickel, manganese, cobalt, platinum, palladium, iridium, aluminum, carbon, nitrogen, and silicon. Accordingly, in certain embodiments, an alloy (e.g., an austenite alloy) useful for making an implantable medical device of the invention contains an austenite promoting component. In certain embodiments, the alloy contains about 10% to about 20%, about 15% to about 25%, about 20% to about 30%, about 25% to about 35%, or about 30% to about 40% of an austenite promoting component. In certain embodiments, the alloy contains at least about 10%, about 12%, about 14%, about 16%, about 18%, about 20%, about 22%, about 24%, about 26%, about 28%, or about 30% of an austenite promoting component. In certain embodiments, the austenite promoting component is calculated as a sum of the percentages of austenite promoting elements (e.g., nickel, cobalt, manganese, platinum, palladium, iridium, aluminum, carbon, nitrogen, silicon, etc.) in the alloy. In other embodiments, the austenite promoting component is a weighted sum of the austenite promoting elements in the alloy. In certain embodiments, individual elements in the weighted sum are weighted according to their austenite promoting efficacy, as compared to nickel. In certain embodiments, the weighted % austenite promoting component is calculated according to the formula: % nickel+% platinum+% palladium+% iridium+0.5×(% manganese+% cobalt)+30×(% carbon+% nitrogen). In certain embodiments, the alloy contains a weighted % austenite promoting component of about 15% to about 25% (e.g., about 16%, about 17%, about 18%, about 19%, about 20%, about 21%, about 22%, about 23%, about 24%, or about 25%). In certain embodiments, the alloy contains an unweighted % austenite promoting component of about 25% to about 35% (e.g., about 28%, about 29%, about 30%, about 31%, about 32%, about 33%, about 34%, or about 35%).

In certain embodiments, an iron reactive component containing alloy (e.g., an austenite alloy containing an iron reactive component) useful for making an implantable medical device of the invention contains less than about 5.0% (e.g., about 0.1% to about 2.5%, about 0.5% to about 3.0%, about 1.0% to about 3.5%, about 1.5% to about 4.0%, or about 2.0% to about 4.5%) of platinum, iridium, and osmium, either individually or in total. In certain embodiments, the alloy contains substantially no platinum, palladium, or iridium. As used herein, "substantially no" platinum, palladium, or iridium means that the alloy contains less than 0.1% of platinum, palladium, or iridium. In certain embodiments, the alloy contains substantially no platinum, palladium, and iridium. In certain embodiments, the alloys contain less than about 0.05%, or about 0.01% of each of platinum, palladium, or iridium. In certain embodiments, the alloys contain less than about 0.05%, or less than about 0.01%, of each of platinum, palladium, and iridium. In other embodiments, the total amount of platinum, iridium, and osmium in the alloy is about 5.0% or greater, and the alloy further comprises at least one additional metal element other than iron, manganese, platinum, iridium, and osmium (e.g., at least about 0.5% or more of said at least one additional metal element). In certain embodiments, the at least one addition metal element is a corrosion resisting element (e.g., chromium, molybdenum, tungsten, titanium, tantalum, niobium, zirconium, or hafnium) or a austenite promoting element selected from the group consisting of nickel, cobalt, and aluminum.

Biodegradable iron reactive component containing alloys implanted in a human or animal body need to be relatively non-toxic because all of the elements in the alloys will eventually be dissolved into body fluids. Nickel is often used to stabilize an austenitic crystal structure. However, many people have nickel allergies and cannot tolerate nickel ions in their systems. Having nickel as part of a biodegradable alloy guarantees that all of the nickel in the alloy will eventually be absorbed by the host's body, which can cause complications in a nickel sensitive individual. Likewise, chromium, cobalt, and vanadium have some toxicity in the human body, and should be minimized in a biodegradable alloy. Accordingly, in certain embodiments, an alloy useful for making a biodegradable implantable medical device of the invention (e.g., an austenite alloy) contains less than about 9.0%, about 8.0%, about 7.0%, about 6.0%, about 5.0%, about 4.0%, about 3.0%, about 2.5%, about 2.0%, about 1.5%, about 1.0%, or about 0.5% of each of nickel, vanadium, chromium, and cobalt. In certain embodiments, the alloy contains substantially no nickel. As used here, the phrase "substantially no nickel" means that the alloy contains 0.1% or less nickel. In certain embodiments, the alloy contains less than about 0.05%, less than about 0.02%, or less than about 0.01% nickel. In certain embodiments, the alloy contains substantially no vanadium. As used here, the phrase "substantially no vanadium" means that the alloy contains 0.1% or less vanadium. In certain embodiments, the alloy contains less than about 0.05%, less than about 0.02%, or less than about 0.01% vanadium. In certain embodiments, the alloy contains less than about 4.0% chromium (e.g., less than about 3.0%, about 2.0%, or about 1.5%). In certain embodiments, the alloy contains substantially no chromium. As used here, the phrase "substantially no" chromium means that the alloy contains 0.1% or less chromium. In certain embodiments, the alloy contains less than about 0.05%, less than about 0.02%, or less than about 0.01% chromium. In certain embodiments, the alloy contains less than about 6.0% (e.g., less than about 5.0%, about 4.0%, about 3.0%, about 2.0%, or about 1.0%) cobalt.

To remove or minimize toxic elements from the alloys used to created the biodegradable implantable medical devices of the invention, the toxic elements can be replaced with non-toxic counterparts. For example, since nickel is used as an austenite promoting element, it can be replaced with other austenite promoting elements, such as manganese, cobalt, platinum, palladium, iridium, aluminum, carbon, nitrogen, and silicon. Similarly, since chromium is used as a corrosion resisting element, it can be replaced with other corrosion resisting elements, such as molybdenum, tungsten, titanium, tantalum, niobium, zirconium, and hafnium. However, not all alloy substitutions are equivalent. For a corrosion resisting effect, molybdenum is as effective as chromium, while niobium and tantalum are only half as effective as chromium, and titanium is twice as effective as chromium. For austenite promoting effect, manganese and cobalt are only half as effective as nickel, while carbon is 30 times more effective than nickel, and nitrogen is 25-30 times more effective than nickel. Accordingly, in certain embodiments, a biodegradable alloy is rendered non-allergenic or less allergenic by replacing one part of nickel with two parts manganese, one part of manganese and one part of cobalt, or two parts of cobalt. In other embodiments, a biodegradable alloy is rendered non-toxic or less toxic by replacing one part of chromium with one part of molybdenum, half a part of titanium, or two parts of tantalum or niobium. In some embodiments, the total percentage of manganese is from about 10% to about 50%, about 15% to about 45%, or about 20% to about 40%, about 25% to about 35%, or about 25% to about 30%, or about 30%. In certain embodiments, the total percentage of nickel, cobalt and manganese is from about 10% to about 50%, about 15% to about 45%, or about 20% to about 40%, about 25% to about 35%, or about 25% to about 30%, wherein the percentage of nickel is less than about 9.0%, about 8.0%, about 7.0%, about 6.0%, about 5.0%, about 4.0%, or about 3.0%. In other embodiments, the total percentage of chromium and molybdenum is from about 1.0% to about 7.0%, about 2.0% to about 8.0%, about 3.0% to about 9.0%, or about 4.0% to about 10%, wherein the amount of chromium is less than about 2.0%, about 1.5%, about 1.0%, or about 0.5%.

Additional elements that can be included in alloys useful for making biodegradable, implantable medical devices of the invention include rhodium, rhenium, and osmium. In certain embodiments, the amount of rhodium, rhenium, or osmium in the alloy is less than about 5.0% (e.g., about 0.1% to about 2.5%, about 0.5% to about 3.0%, about 1.0% to about 3.5%, about 1.5% to about 4.0%, or about 2.0% to about 4.5%). In certain embodiments, there is substantially no rhodium, rhenium, or osmium in the alloy. As used herein, "substantially no" rhodium, rhenium, or osmium means that the alloy contains less than about 0.1% of rhodium, rhenium, or osmium. In certain embodiments, there is substantially no rhodium, rhenium, and osmium in the alloy. In certain embodiments, the alloy contains less than about 0.05%, or less than about 0.01%, of rhodium, rhenium, or osmium. In certain embodiments, the alloy contains less than about 0.05%, or less than about 0.01%, of each of rhodium, rhenium, and osmium.

In certain embodiments, when one or more elements selected from the group consisting of platinum, palladium, iridium, rhodium, rhenium, and osmium is present in an alloy useful for making biodegradable, implantable medical devices of the invention, the amount of manganese in the alloy is less than about 5.0% (e.g., less than about 4.5%, about 4.0%, about 3.5%, about 3.0%, or about 2.5%). In other embodiments, when one or more elements selected from the group consisting of platinum, palladium, iridium, rhenium, rubidium, and osmium is present in the alloy and the amount of manganese in the alloy is about 5.0% or greater (e.g., about 5.0% to about 30%), then the alloy further comprises at least one additional metal element. In certain embodiments, the at least one addition metal element is a corrosion resisting element (e.g., chromium, molybdenum, tungsten, titanium, tantalum, niobium, zirconium, or hafnium) or a austenite promoting element selected from the group consisting of nickel, cobalt, and aluminum.

In certain embodiments, alloys useful for making biodegradable, implantable medical devices of the invention contain substantially no rubidium or phosphorus. As used herein, "substantially no" rubidium or phosphorus means less than 0.1% of rubidium of phosphorus. In certain embodiments, the alloys contain substantially none rubidium and phosphorus. In certain embodiments, the alloys contain less than about 0.05%, or less than about 0.01%, of rubidium or phosphorus. In certain embodiments, the alloys contain less than about 0.05%, or less than about 0.01%, of each of rubidium and phosphorus.

In certain embodiments, the present invention provides biodegradable implantable medical devices comprising a range of biodegradable alloys (e.g., austenitic alloys) that are acceptably non-allergenic, non-toxic, has little or no magnetic susceptibility and low magnetic permeability, and provide a useful range of degradation rates. The following are exemplary boundaries defining alloys useful in the biodegradable implantable medical devices of the present invention:
an iron reactive component;
substantially no nickel;
substantially no vanadium;
less than about 6.0% chromium;
less than about 10% cobalt;
a corrosion resisting component of less than about 10% (e.g., about 0.5% to about 10%); and
an austenite promoting component of at least about 10% (e.g., about 10% to about 40%).

In certain embodiments, the present invention provides biodegradable implantable medical devices comprising a range of biodegradable alloys (e.g., austenitic alloys) that are acceptably non-allergenic, non-toxic, has little or no magnetic susceptibility and low magnetic permeability, and provide a useful range of degradation rates. The following are exemplary boundaries defining alloys useful in the biodegradable implantable medical devices of the present invention:
an iron reactive component;
28%-30% manganese;
0.07%-0.09% carbon;
0.18%-0.22% Niobium;
a corrosion resisting component of less than about 10% (e.g., about 0.5% to about 10%); and
an austenite promoting component of at least about 10% (e.g., about 10% to about 40%).

In certain embodiments, the present invention provides biodegradable implantable medical devices comprising a range of biodegradable alloys (e.g., austenitic alloys) that are acceptably non-allergenic, non-toxic, has little or no magnetic susceptibility and low magnetic permeability, and provide a useful range of degradation rates. The following are exemplary boundaries defining alloys useful in the biodegradable implantable medical devices of the present invention:
an iron reactive component;
28%-30% manganese;
0.18%-0.22% niobium;
<0.01% carbon;
a corrosion resisting component of less than about 10% (e.g., about 0.5% to about 10%); and
an austenite promoting component of at least about 10% (e.g., about 10% to about 40%).

In certain embodiments, the present invention provides biodegradable implantable medical devices comprising a range of biodegradable alloys (e.g., austenitic alloys) that are acceptably non-allergenic, non-toxic, has little or no magnetic susceptibility and low magnetic permeability, and provide a useful range of degradation rates. The following are exemplary boundaries defining alloys useful in the biodegradable implantable medical devices of the present invention:
an iron reactive component;
28-30% manganese;
0.07-0.09% carbon;
a corrosion resisting component of less than about 10% (e.g., about 0.5% to about 10%); and
an austenite promoting component of at least about 10% (e.g., about 10% to about 40%).

In certain embodiments, the alloys contain about 55% to about 80% iron. For example, in certain embodiments, the alloys contain about 55% to about 65%, about 60% to about 70%, about 65% to about 75%, about 70% to about 80% iron. In certain embodiments, the amount of chromium is less than about 4.0% and the amount of cobalt is less than about 6.0%. In certain embodiments, the amount of chromium is less than about 2.0 and the amount of cobalt is less than about 4.0%. In certain embodiments, the corrosion resisting component is less than about 8.0% (e.g., about 0.5% to about 8.0%) and the austenite promoting component is greater than about 12%. In certain embodiments, the corrosion resisting component is less than less than about 7.0% (e.g., about 0.5% to about 7.0%) and the austenite promoting component is greater than about 14%. In certain embodiments, the corrosion resisting component is less than about 6.0% (e.g., about 0.5% to about 6.0%) and the austenite promoting component is greater than about 16%. In certain embodiments, the corrosion resisting and austenite promoting components are calculated as sums of the percentages of corrosion resisting and austenite promoting elements, respectively. In other embodiments, the corrosion resisting and austenite promoting components are calculated as weighted sums of the corrosion resisting and austenite promoting elements, respectively. In certain embodiments, the weighted % corrosion resisting component is determined according to the formula: % chromium+% molybdenum+% tungsten+0.5×(% tantalum+% niobium)+2×(% titanium+% zirconium+% hafnium). In certain embodiments, the weighted % austenite promoting component is calculated according to the formula: % nickel+% platinum+% palladium+% iridium+0.5×(% manganese+% cobalt)+30×(% carbon+% nitrogen). In certain embodiments, the alloys contain less than about 5.0% manganese (e.g., less than about 4.5%, about 4.0%, about 3.5%, about 3.0%, or about 2.5%). In certain embodiments, the alloys contain one or more elements selected from the group consisting of platinum, palladium, iridium, rhodium, rhenium, and osmium. In certain embodiments, the alloys contain about 0.5% to about 5.0% of one or more elements selected from the group consisting of platinum, palladium, iridium, rhodium, rhenium, and osmium. In certain embodiments, the alloys contain substantially none of the elements selected from the group consisting of platinum, palladium, iridium, rhodium, rhenium, and osmium. In certain embodiments, the alloys contain substantially none of the elements selected from the group consisting of rubidium and phosphorus.

The biodegradation rate of the implantable medical devices of the present invention is enhanced by the presence of the iron reactive component in the alloy. As such, the incorporation of a halogen component into the alloy of an implantable medical device provides a novel method for enhancing biodegradation. In some embodiments, the alloy containing the iron reactive component reacts with a bodily fluid when it is in contact with the fluid. In some embodiments, the degradation rate of the alloy comprising the iron reactive component when implanted in a biological subject is faster than the degradation rate of an alloy having the same composition as except the iron reactive component is absent. In some embodiments, the implantable medical devices of the present invention have a degradation rate of about 1-100 mg per day per square inch, about 1-50 mg per day per square inch, about 1-20 mg per day per square inch, about 1-10 mg per day per square inch, about 1-5 mg per day per square inch, or about 1-1.5 mg per day per square inch when placed in pure water or a solution that does not contain a halogen component. In some embodiments, the implantable medical devices of the present invention have a degradation rate of about 1-2 mg per day per square inch when placed in pure water or a solution that does not contain a halogen component. In some embodiments, the implantable medical devices of the present invention have a degradation rate of about 1.2 mg per day per square inch and 1.4 mg per day per square inch. The degradation rate of biodegradable materials in a human or animal body is a function of the environment surrounding the implantable medical device.

In embodiments where the iron reactive component is a halogen component, the degradation of the biodegradable material in an environment containing a halogen is faster than in an environment with lower concentrations of halogen or lacking a halogen (i.e., a halogen poor or absent environment). Halogens in the environment speed the degradation of the implantable medical device, but do not become part of the degradation products, which include oxides, phosphates and carbonates. The biodegradation rate is further enhanced by the presence of a halogen in the solution in which the implantable medical device is immersed. In some embodiments, the biodegradation rate is enhanced by the presence of the halogen component in the alloy. In some embodiments, the biodegradation rate is enhanced by the presence of the halogen component on the exterior of the implantable medical device.

The degradation of an entire implant is an additionally a function of the mass of the implant as compared to its surface area. Implants come in many different sizes and shapes. A typical coronary stent, for example, weighs 0.0186 grams and has a surface area of 0.1584 square-inches. At a degradation rate of 1 mg/square-inch/day, a coronary stent would loose 50% of its mass in 30 days. In comparison, a 12 mm long cannulated bone screw weighs 0.5235 g and has a surface area of 0.6565 square-inches. At the same degradation rate of 1 mg/square-inch/day, the cannulated screw will loose half of its mass in 363 days. Thus, as persons skilled in the art will readily appreciate, it is desirable to have biodegradable alloys that have a range of degradation rates to accommodate the variety of implants used in the body of a subject.

In addition, the biodegradation rate of the implantable medical devices of the present invention are significantly influenced by the transport characteristics of the surrounding tissue. For example, the biodegradation rate of an implant placed into bone, where transport to the rest of the body is limited by the lack of fluid flow, would be slower than a vascular stent device that is exposed to flowing blood. Similarly, a biodegradable device embedded in tissue would have slower degradation rate than a device exposed to flowing blood, albeit a faster degradation rate than if the device was embedded in bone. Moreover, different ends of a medical device could experience different rates of degradation if, for example, one end is located in bone and the other end is located in tissue or blood. Modulation of biodegradation rates based on the location of the device and ultimate device requirements is thus desirable.

In order to control the dissolution rate of a medical device independent of the geometric shape changes that occur as the device degrades, several techniques have been developed. The first method to alter the dissolution profile of a metallic device is to alter the geometry of the device such that large changes in surface area are neutralized. For example, the surface to mass ratio can be increased or maximized. A substantially cylindrical device, which would lose surface area linearly with the loss of diameter as the device degrades, could have a concentric hole drilled through the center of the device. The resulting cavity would cause a compensating increase in surface area as alloy was dissolved from the luminal surface of the device. As a result, the change in surface area as the device degrades over time—and thus the change in rate of degradation—would be minimized or eliminated. A similar strategy of creating a luminal space (e.g., a luminal space that has a shape similar to the outer surface of the device) could be implemented with essentially any type of medical device.

Because biodegradation rates are partially a function of exposure to bodily fluid flow, biodegradation rates can be modified by coating (e.g., all or part of) the biodegradable implantable medical device with a substance that protects the alloy surface. For example, biodegradable hydrogels, such as disclosed in U.S. Pat. No. 6,368,356, could be used to retard exposure of any parts of a device exposed to mobile bodily fluids, thereby retard dissolution and transport of metal ions away from the device. Alternatively, medical devices can be constructed with two or more different alloys described herein, wherein parts of the device that are exposed to mobile bodily fluids are made from more corrosion resistant alloys (i.e., alloys comprising higher amounts of a corrosion resisting component), while parts of the device imbedded in bone or tissue are made from less corrosion resistant alloys. In certain embodiments, the different parts of the device can be made entirely from different alloys. In other embodiments, parts of the device exposed to mobile bodily fluids can have a thin layer or coating of an alloy that is more corrosion resistant than the alloy used to make the bulk of the device.

It is frequently desirable to incorporate bioactive agents (e.g., drugs) on implantable medical devices. For example, U.S. Pat. No. 6,649,631 claims a drug for the promotion of bone growth which can be used with orthopedic implants. Bioactive agents may be incorporated directly on the surface of an implantable medical device of the invention. For example, the agents can be mixed with a polymeric coating, such as a hydrogel of U.S. Pat. No. 6,368,356, and the polymeric coating can be applied to the surface of the device. Alternatively, the bioactive agents can be loaded into cavities or pores in the medical devices which act as depots such that the agents are slowly released over time. The pores can be on the surface of the medical devices, allowing for relatively quick release of the drugs, or part of the gross structure of the alloy used to make the medical device, such that bioactive agents are released gradually during most or all of the useful life of the device. The bioactive agents can be, e.g., peptides, nucleic acids, hormones, chemical drugs, or other biological agents, useful for enhancing the healing process.

As persons skilled in the art will readily recognize, there are a wide array of implantable medical devices that can be made using the alloys disclosed herein. In certain embodiments, the implantable medical device is a high tensile bone anchor (e.g., for the repair of separated bone segments). In other embodiments, the implantable medical device is a high tensile bone screw (e.g., for fastening fractured bone segments). In other embodiments, the implantable medical device is a high strength bone immobilization device (e.g., for large bones). In other embodiments, the implantable medical device is a staple for fastening tissue. In other embodiments, the implantable medical device is a craniomaxillofacial reconstruction plate or fastener. In other embodiments, the implantable medical device is a dental implant (e.g., a reconstructive dental implant). In still other embodiments, the implantable medical device is a stent (e.g., for maintaining the lumen of an opening in an organ of an animal body).

Powdered metal technologies are well known to the medical device community. Bone fasteners having complex shapes are fabricated by high pressure molding of a powdered metal in a carrier, followed by high temperature sintering to bind the metal particles together and remove the residual carrier. Powdered metal devices are typically fabricated from nonreactive metals such as 316LS stainless steel. The porosity of the finished device is partially a function of the metal particle size used to fabricate the part. Because the metal particles are much larger and structurally independent of the grains in the metal's crystal structure, metal particles (and devices made from such particles) can be made from alloys of any grain size. Thus, biodegradable implantable medical devices of the invention can be fabricated from powders made from any of the alloys described herein. The porosity resulting from the powdered-metal manufacturing technique, can be exploited, for example, by filling the pores of the medical devices with biodegradable polymers. The polymers can be used to retard the biodegradation rates of all or part of the implanted device, and/or mixed with bioactive agents (e.g., drugs) that enhance the healing of the tissue surrounding the device. If the porosity of the powdered metal device is filled with a drug, the drug will be delivered as it becomes exposed by the degradation of the device, thereby providing drug to the tissue site as long as the device remains present and biodegrading.

In certain embodiments, the implantable medical device is designed for implantation into a human. In other embodiments, the implantable medical device is designed for implantation into a pet (e.g., a dog, a cat). In other embodiments, the implantable medical device is designed for implantation into a farm animal (e.g., a cow, a horse, a sheep, a pig, etc.). In still other embodiments, the implantable medical device is designed for implantation into a zoo animal.

In another aspect, the invention provides a container containing an implantable medical device of the invention. In certain embodiments, the container is a packaging container, such as a box (e.g., a box for storing, selling, or shipping the device). In certain embodiments, the container further comprises an instruction (e.g., for using the implantable medical device for a medical procedure).

All publications, patent applications, and issued patents cited in this specification are herein incorporated by reference as if each individual publication, patent application, or issued patent were specifically and individually indicated to be incorporated by reference in its entirety.

The following examples are intended to illustrate, but not to limit, the invention in any manner, shape, or form, either explicitly or implicitly. While the specific alloys described exemplify alloys that could be used in implantable medical devices of the invention, persons skilled in the art will be able to readily identify other suitable alloys in light of the present specification. Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of non-critical parameters that could be changed or modified to yield essentially similar results.

EXAMPLES

Example 1

Background: Biodegradable metal systems have been developed for use in cardiovascular, orthopedic, surgical and other applications. The advantage of biodegradable metals are that they have high strength and are dissolved by the body and excreted over time until they are completely eliminated from the body. These materials are extremely useful where an implant is needed for a short period of time, such as for bone fixation or artery repair, and can have negative impacts after healing has take place at the implant site. Stents can cause a stenotic lesion if left in place long after they no longer serve a function and bone fixation devices can cause long term discomfort and are frequently removed after they are no longer required. An example of a biodegradable metal system is U.S. Pat. No. 8,246,762 which discloses biodegradable metals for implant that degrade from the surface and consequently do not lose bulk properties of the non-degraded portion of the implant.

The degradation performance of biodegradable materials in a human or animal body is a function of the environment surrounding the implant. The degradation of the biodegradable material in an environment containing sodium or potassium chloride is faster than in a sodium or potassium chloride poor environment. Chloride in the environment speeds the degradation but does not become part of the degradation products, which are normally oxides, phosphates and carbonates. Degradation in areas directly exposed to a flow of body fluid, such as blood, bile, bone marrow or lymph, is faster than material imbedded in tissue or bone, where the flow of fluids required for the degradation reactions are transported across cellular membranes to the implant. As more fluid and chloride are transported to the site of the implant, the biodegradation becomes faster and degraded material can be transported away from the site more quickly.

One such material is an iron alloy that contains 28% Manganese, 0.2% niobium, 0.08% carbon and the balance iron. When placed in a solution of saline 0.9% sodium chloride in water (normal saline), the material degrades at a rate of 1.2 mg per day per square inch of surface. A sample of the material 0.69 inches long by 0.39 inches wide by 0.025 inches thick was placed in purified water for 123 days. The sample lost 0.7 mg per day per square inch of surface, approximately half of the saline degradation rate. When implanted in the body and surrounded by tissue or bone, the degradation of the material is dependent on the amount and content of the bodily fluid transported to and away from the implant site and degradation is slowed. However, if the chloride content at the implant surface can be increased, the degradation rate can be increased.

Disclosure: It has been found that the degradation profile of iron based metals can be altered by including materials that are reactive with iron based alloys into the alloy at the time it is made or added to the surface of the alloy after it is final formed. Iron based alloys react with chloride ions in solution as is demonstrated by increased degradation of alloys in saline solution as compared with purified water. Some body fluids can become chloride deficient. Adding chloride to the alloy causes the chloride located at the surface or the alloy to react with the alloy when it comes in contact with a fluid regardless of the fluid composition. In addition, the chloride at the surface of the alloy upsets the osmotic equilibrium at the site causing an increase in fluid migrating to the site. It is not just chloride ion that increases the degradation of iron based compounds, the other halogens such as fluoride and iodide and bromide have the same effect.

Adding halogens to an alloy can be accomplished by adding small amounts of halogen compounds, which have boiling points above the melting temperature of the alloy mix at the time it is melted. In some embodiments, the halogen compound is stable on heating to alloying temperatures and capable of being dispersed in the alloy without appreciable segregating at the grain boundaries. Examples of useful compounds are sodium fluoride, sodium chloride, copper chloride, silver chloride, calcium chloride and iron chloride.

Four ingots of approximately 28% manganese, 0.2% niobium, 0.08% carbon and the balance iron were fabricated with the addition of 100 ppm of chloride from one of sodium chloride, calcium chloride, sodium fluoride and copper chloride salts. The fabricated ingots were hot worked and cold rolled to approximately 0.025 inches thick. Samples of each ingot were placed in purified water with no chloride or fluoride present and experienced degradation rates of between 1.2 mg per day per square inch and 1.4 mg per day per square inch of sample—essentially the expected degradation rate in saline of the base material without the addition of a chloride source.

Alternatively, a halogen may be applied to the exterior surface of an alloy or an implant fabricated from an alloy by ion-implanting the surface with a halogen such as chlorine or fluorine. Ion-implanting is a well understood process that is practiced on large scale to modify the chemical structure and properties of semiconductors and metals. By ion-implanting a halogen onto the surface structure of a metal, the reaction at the surface can be moderated and because the halogen is not consumed by the degradation products, it is available to continue the degradation process as long as it is not transported away from the site.

Samples of an alloy consisting of 28% manganese, 0.2% niobium, 0.08% carbon and the balance iron was electropolished, fastened to a silicon wafer and the surface successfully implanted with $10^{15}$ molecules of chlorine at an accelerating voltage of 100 key. The experiment was repeated with fluorine. Each sample had one side implanted with either a chlorine and fluorine and the reverse side was left as native alloy. The samples were placed in distilled water and examined twice daily. The halogen implanted surface began to degrade in one day while the native surface took several days.

Example 2

Fabrication of a biodegradable material with enhanced degradation rates may be facilitated through the use of a partial pressure of a gaseous reactive component during the fabrication process. For example, a procedure for the initial fabrication of a metal alloy is to place some or all of the desired components of the alloy into the crucible of a vacuum induction furnace, evacuate the furnace and melt the components under vacuum and/or with a partial pressure of argon. Without being bound to any particular theory, it is recognized in the present invention a partial pressure of argon can be used to minimize evaporative loss of the desired components and to prevent metal plasma forming in the furnace chamber which would cause damage to the furnace. After the alloy is fully melted and mixed, it is poured into a mold and cooled.

In some embodiments, it is desirable to add the some components of the metal alloy at a later stage of the melting process. To add components to the melt they are contained separately in an addition chamber and released into the crucible at the appropriate time. The reactive components of this invention in some embodiments can be added later in the melting process, prior to the melt being poured into the mold. In some embodiments, the amount of reactive component in the melt can be better controlled by using a partial pressure of the reactive component in the vacuum chamber surrounding the melt. The partial pressure of the reactive component can have a chemical activity approximately equal to the chemical activity of the reactive component in the melt. The partial pressure of the reactive component can either be used to replace the partial pressure of argon or be added to the partial pressure of argon. The latter would provide a higher total pressure surrounding the melt and would further reduce loss by evaporation.

An example of this procedure is the melting of the main alloy components of Iron, Manganese, Niobium and carbon under vacuum followed by the addition of argon at a partial pressure of 200 torr. At the appropriate time in the melt process, the partial pressure in the chamber is increased with the addition of chlorine gas of approximately 1 torr and the reactive chloride salts are released into the melt from the addition chamber. The melt is allowed to mix and poured into the mold for cooling.

Although the invention has been described with reference to the presently preferred embodiments, it should be understood that various changes and modifications, as would be obvious to one skilled in the art, can be made without departing from the spirit of the invention. Accordingly, the invention is limited only by the following claims.

What is claimed:

1. A method of producing a biodegradable alloy that is austenitic in structure and includes iron, at least one additional metallic element, and an iron reactive component, wherein the iron reactive component is dispersed within the biodegradable alloy at a concentration between about 0.1 ppm to about 500 ppm, and wherein the degradation rate of the biodegradable alloy, when implanted in a biological subject, is greater than the degradation rate of an alloy having the same composition as the biodegradable alloy except the absence of the iron reactive component, the method comprising:
   melting iron, the at least one additional metallic element, and a salt containing the iron reactive component to produce a mixture; and
   contacting the mixture with a gas containing the iron reactive component to produce the biodegradable alloy.

2. The method of claim 1, wherein the salt containing the iron reactive component is selected from the group consisting of sodium fluoride, sodium chloride, copper chloride, copper fluoride, magnesium chloride, silver chloride, calcium chloride, calcium fluoride, iron chloride, and a combination thereof.

3. The method of claim 1, wherein the gas containing the iron reactive component has a partial pressure of at least about 0.1 torr, at least about 0.2 torr, at least about 0.5 torr, at least about 0.8 torr, at least about 1 torr, at least about 2 torr, at least about 5 torr, at least about 10 torr, at least about 50 torr, or at least about 100 torr.

4. The method of claim 1, the iron reactive component is a halogen component.

5. The method of claim 4, wherein the halogen component is selected from the group consisting of chloride, fluoride, bromide, and iodide.

6. The method of claim 5, wherein the halogen component is chloride or fluoride.

7. The method of claim 5, wherein the gas containing the iron reactive component is selected from the group consisting of chlorine, fluorine, bromine, and iodine.

8. The method of claim 1, further comprising mixing the iron reactive component with argon gas to produce the gas containing the iron reactive component.

9. The method of claim 8, wherein the argon gas has a partial pressure of at least about 10 torr, at least about 20 torr, at least about 50 torr, at least about 80 torr, at least about 100 torr, at least about 150 torr, at least about 200 torr, at least about 250 torr, at least about 300 torr, or at least about 500 torr.

10. The method of claim 1, wherein the biodegradable alloy includes an austenite-promoting component and a corrosion-resisting component.

11. The method of claim 1, wherein the biodegradable alloy contains between about 20% to 40% manganese by weight.

12. The method of claim 1, wherein the biodegradable alloy contains less than about 0.3% niobium by weight.

13. The method of claim 1, wherein the biodegradable alloy contains less than about 1% carbon by weight.

14. The method of claim 1, wherein the biodegradable alloy includes manganese and niobium.

15. The method of claim 1, wherein the biodegradable alloy includes at least about 0.01% to about 0.1% a non-metallic element by weight.

16. The method of claim 15, wherein the biodegradable alloy includes at least about 0.01% to about 0.1% carbon by weight.

17. The method of claim 1, wherein the biodegradable alloy is in a form of an implantable medical device.

18. The method of claim 17, wherein the implantable medical device is a bone screw, a bone anchor, a tissue staple, a craniomaxillofacial reconstruction plate, a fastener, a reconstructive dental implant, or a stent.

19. The method of claim 17, further comprising coating the implantable medical device with a therapeutic agent.

20. The method of claim 17, further comprising coating the implantable medical device with a biodegradable hydrogel.

21. The method of claim 17, wherein the implantable medical device has a geometry that maximizes the surface to mass ratio.

22. The method of claim 17, wherein the implantable medical device includes a hollow opening or passageway formed therein.

23. The method of claim 1, wherein the concentration of the iron reactive component in the biodegradable alloy is between about 1 ppm to about 500 ppm, between about 10 ppm to about 300 ppm, or between about 50 ppm to about 150 ppm.

24. The method of claim 1, wherein the concentration of the iron reactive component in the biodegradable alloy is about 200 ppm.

25. The method of claim 1, wherein the iron, the at least one additional metallic element, and the salt containing the iron reactive component are melted in the presence of the gas containing the iron reactive component.

26. A biodegradable alloy produced by the method of claim 1.

* * * * *